(12) United States Patent
Dertinger et al.

(10) Patent No.: US 9,133,505 B2
(45) Date of Patent: Sep. 15, 2015

(54) RAPID IN VIVO GENE MUTATION ASSAY BASED ON THE PIG-A GENE

(75) Inventors: Stephen D. Dertinger, Webster, NY (US); Steven M. Bryce, Rochester, NY (US)

(73) Assignee: Litron Laboratories, Ltd., Rochester, NY (US)

( * ) Notice: Subject to any disclaimer, the term of this patent is extended or adjusted under 35 U.S.C. 154(b) by 0 days.

(21) Appl. No.: 13/304,179

(22) Filed: Nov. 23, 2011

(65) Prior Publication Data
US 2012/0129160 A1   May 24, 2012

Related U.S. Application Data

(60) Provisional application No. 61/417,104, filed on Nov. 24, 2010.

(51) Int. Cl.
*G01N 33/53* (2006.01)
*C12Q 1/68* (2006.01)

(52) U.S. Cl.
CPC .................................... *C12Q 1/6827* (2013.01)

(58) Field of Classification Search
CPC ..... G01N 33/00; G01N 33/53; G01N 33/537; G01N 33/555; G01N 33/5014; G01N 2333/70596; G01N 2333/70557; G01N 33/54326; C12Q 1/6827; C12Q 2563/131; C12Q 2563/143; C12Q 2563/149; C12Q 2565/626; C12Q 2563/107
See application file for complete search history.

(56) References Cited

U.S. PATENT DOCUMENTS

| | | | |
|---|---|---|---|
| 4,444,879 | A | 4/1984 | Foster et al. |
| 5,314,805 | A | 5/1994 | Haugland et al. |
| 5,858,667 | A | 1/1999 | Dertinger et al. |
| 6,100,038 | A | 8/2000 | Dertinger et al. |
| 6,593,095 | B1 | 7/2003 | Buckley et al. |
| 6,933,148 | B2 * | 8/2005 | Collins et al. ................. 435/372 |
| 7,358,059 | B2 | 4/2008 | Orfao De Matos Correia e Vale |
| 7,824,874 | B2 | 11/2010 | Dertinger |
| 2003/0138851 | A1 | 7/2003 | De Matos et al. |
| 2004/0229785 | A1 * | 11/2004 | Faustman ........................ 514/12 |
| 2005/0042602 | A1 | 2/2005 | Ahearn et al. |
| 2006/0040291 | A1 | 2/2006 | Dertinger et al. |
| 2006/0140963 | A1 | 6/2006 | Young et al. |
| 2007/0274919 | A1 | 11/2007 | Dertinger |
| 2009/0311706 | A1 | 12/2009 | Dertinger |
| 2011/0027793 | A1 | 2/2011 | Dertinger |

FOREIGN PATENT DOCUMENTS

WO        99/36778 A1      7/1999

OTHER PUBLICATIONS

Offer et al., FASEB J 19(3):485-7, Epub Dec. 15, 2004.*
Belvedere et al., Blood cells, Molecules, and Disease 25(9): 141-146, 1999.*
Dertinger et al., "Integration of Mutation and Chromosomal Damage Endpoints into 28-Day Repeat Dose Toxicology Studies," Toxicol. Sci. 115(2):401-411 (2010).
Phonethepswath et al., "Pig-a Mutation: Kinetics in Rat Erythrocytes Following Exposure to Five Prototypical Mutagens," Toxicol. Sci. 114(1):59-70 (2010).
Dertinger et al., "When Pigs Fly: Immunomagnetic Separation Facilitates Rapid Determination of Pig-a Mutant Frequency by Flow Cytometric Analysis," Mut. Res. 721:163-170 (2011).
Parker et al., "Diagnosis and Management of Paroxysmal Nocturnal Hemoglobinuria," Blood 106(12):3699-3709 (2005).
Bryce et al., "In vivo Mutation Assay Based on the Endogenous Pig-a Locus," Environ. Mol. Mutagen 49(4):256-264 (2008).
Albertini, "Somatic Mutation Models of Relevance for Humans," Environmental Mutagen Society, Meeting Abstracts, No. 8 (p. 161) (May 2003).
Miura et al., "Development of an In Vivo Gene Mutation Assay Using the Endogenous Pig-A Gene: I. Flow Cytometric Detection of CD59-Negative Peripheral Red Blood Cells and CD48-Negative Spleen T-Cells from the Rat," Environ. Mol. Mutagen 49:614-621 (2008).
Hernandez-Compo et al., "Quantitative Analysis of the Expression of Glycosylphosphatidylinositol-Anchored Proteins During the Maturation of Different Hematopoietic Cell Compartments of Normal Bone Marrow," Cytometry Part B (Clin. Cytometry) 72B:34-42 (2007).
Chen et al., "Glycophosphatidylinositol-Anchored Protein Deficiency as a Marker of Mutator Phenotypes in Cancer," Cancer Res. 61:654-658 (2001).
Wang et al., "Clinical Significance of a Minor Population of Paroxysmal Nocturnal Hemoglobinuria-Type Cells in Bone Marrow Failure Syndrome," Blood 100(12):3897-3902 (2002).
Ware et al., "Immunophenotypic Analysis of Reticulocytes in Paroxysmal Nocturnal Hemoglobinuria," Blood 86(4):1586-1589 (1995).
Araten et al., "A Quantitative Measurement of the Human Somatic Mutation Rate," Cancer Res. 65(18):8111-8117 (2005).
Ware, Russell E., "Is There a Little PNH in ALL of US?," Blood 105(10):3760-3761 (2005).
Hernandez-Campo et al., "Comparative Analysis of Different Flow Cytometry-Based Immunophenotypic Methods for the Analysis of CD59 and CD55 Expression on Major Peripheral Blood Cell Subsets," Cytometry (Clin. Cytometry) 50:191-201 (2002).
International Search Report and Written Opinion for corresponding PCT/US11/62125 (Mar. 19, 2012).
Phonethepswath et al., "Erythrocyte-Based Pig-a Gene Mutation Assay: Demonstration of Cross-Species Potential," Mutat. Res. 657(2):122-126 (2008).
Araten et al., "Clonal Populations of Hematopoietic Cells with Paroxysmal Nocturnal Hemoglobinuria Genotype and Phenotype are Present in Normal Individuals," Proc. Nat. Acad. Sci. U.S.A. 96:5209-5214 (1999).
Supplementary European Search Report for corresponding European Application No. 11842900 (mailed Mar. 19, 2014).

* cited by examiner

*Primary Examiner* — Phuong Huynh
(74) *Attorney, Agent, or Firm* — LeClairRyan, a Professional Corporation

(57) ABSTRACT

The invention relates to methods and kits for the quantitative analysis of in vivo mutation frequencies of the Pig-A gene in individuals, particularly using peripheral blood samples of vertebrates.

21 Claims, 7 Drawing Sheets

RAPID IN VIVO GENE MUTATION ASSAY BASED ON THE PIG-A GENE

The present application claims the benefit of U.S. Provisional Patent Application Ser. No. 61/417,104, filed Nov. 24, 2010, which is hereby incorporated by reference in its entirety.

This invention was made with government support under grant number R44 ES018017 awarded by the National Institutes of Health-National Institute of Environmental Health Sciences (NIH-NIEHS). The government has certain rights in this invention.

FIELD OF THE INVENTION

The present invention relates to methods and materials for the quantitative analysis of in vivo mutant cell frequencies in individuals, particularly using peripheral blood samples of vertebrates.

BACKGROUND OF THE INVENTION

Several authors have articulated the possibility of using the endogenous Pig-A gene as a reporter of somatic mutation (Araten et al., "Clonal Populations of Hematopoietic Cells with Paroxysmal Nocturnal Hemoglobinuria Genotype and Phenotype are Present in Normal Individuals," Proc Natl Acad Sci USA 96:5209-5214 (1999); Chen et al., "Glycophosphatidylinositol-anchored Protein Deficiency as a Marker of Mutator Phenotypes in Cancer," Cancer Res. 61:654-658 (2001)). As with the HPRT locus, Pig-A is located on the X-chromosome. Iida and colleagues isolated the human genomic gene, and found that it contains six exons over its 17 kb length (Iida et al., "Characterization of Genomic PIG-A Gene: A Gene for GPI Anchor Biosynthesis and Paroxysmal Nocturnal Hemoglobinuria," Blood 83:3126-3131 (1994)). As demonstrated by Kawagoe et al., "Molecular cloning of Murine pig-a, a Gene for GPI-anchor Biosynthesis, and Demonstration of Interspecies Conservation of its Structure, Function, and Genetic Locus," Genomics 23:566-574 (1994), there is a high degree of interspecies conservation of the gene's structure, function, and locus. The Pig-A gene product acts in the first step in glycosylphosphatidylinositol (GPI) anchor biosynthesis, and the entire process is thought to require at least 12 genes. Mutation of any one of these could theoretically result in GPI anchor deficiency. However, all other genes involved in GPI anchor synthesis are autosomal. Mutations on both alleles would have to occur to ablate expression of GPI anchors, and this is expected to be a very rare event. Thus, an inability to anchor GPI-linked proteins in the outer membrane is believed to be virtually equivalent to Pig-A mutation.

This key assumption, as well as practical aspects of assay development, greatly benefit from research on Paroxysmal Nocturnal Hemoglobinuria (PNH). PNH is a genetic disorder that affects 1 to 10 per million individuals, and is caused by a somatic Pig-A gene mutation within a bone marrow stem cell (Norris et al., "The Defect in Glycosylphosphatidylinositol Anchor Synthesis in Paroxysmal Nocturnal Hemoglobinuria," Blood 83:816-821 (1994)). Since bone marrow stem cells are the precursors for the entire hematopoietic system, the gene mutation tends to affect numerous lineages. Erythrocytes, granulocytes and monocytes are typically affected. In a minority of cases, however, lymphocytes are also affected. A key finding is that all PNH clones to date exhibit mutation at the Pig-A locus (Nishimura et al., "Paroxysmal Nocturnal Hemoglobinuria: An Acquired Genetic Disease," Am J Hematol 62:175-182 (1999)). Furthermore, an analysis of 146 PNH patients by Nishimura and colleagues provides important examples of the types of mutations that lead to GPI anchor deficiency. Single-base substitutions and frame-shift events are the most highly represented classes of mutation observed. Even so, there are three examples of large deletions (entire gene, 4 kb, and 737 base pairs), as well as a large insertion (88 base pairs). The mutations are widely distributed in the coding regions and splice sites, although others have found a somewhat higher frequency of missense mutations in exon 2 relative to other exons (Nafa et al., "The Spectrum of Somatic Mutations in the PIG-A Gene in Paroxysmal Nocturnal Hemoglobinuria Includes Large Deletions and Small Duplications," Blood Cells Mol Dis 24:370-384 (1998)). Taken together, the PNH literature provides strong evidence that an in vivo assay based on the Pig-A gene would be sensitive to each important class of mutation.

In a report by Miura et al., "Development of an In Vivo Gene Mutation Assay Using the Endogenous Pig-A Gene: I. Flow Cytometric Detection of CD59-Negative Peripheral Red Blood Cells and CD48-Negative Spleen T-Cells From the Rat," Environ. Molec. Mutagen. 49:614-621 (2008), a method for quantifying the frequency of mutant phenotype erythrocytes was identified. In that flow cytometry-based assay, anti-CD45 antibody was used to differentiate leukocytes from erythrocytes, and anti-CD59-FITC was used to distinguish mutant phenotype erythrocytes from wild-type erythrocytes. The authors also described a second approach whereby the fluorescent reagent FLAER and flow cytometry could be used to quantify the frequency of mutant phenotype erythrocytes. However, these approaches did not differentiate mature erythrocytes from the immature fraction of erythrocytes (reticulocytes). This is a significant disadvantage of the approach of Miura et al., because differential staining of mature and immature erythrocytes allows one to determine the percentage of reticulocytes among total erythrocytes simultaneously with Pig-A mutation measurements. These percent reticulocyte values provide important information regarding bone marrow toxicity, a parameter that is valuable for interpreting any genotoxicity endpoint that is based on hematopoietic cells. Differentially staining reticulocytes and mature erythrocytes also allows one to measure Pig-A mutation frequency in both the total RBC cohort as well as the reticulocyte fraction. The latter measurement is valuable for some experimental designs, since maximal mutagenic responses are obtained in this fraction of cells sooner than those observed in the total erythrocyte pool. Furthermore, the approach of Miura et al. for distinguishing erythrocytes from leukocytes was less than ideal. Namely, in their hands, anti-CD45 did not afford clear resolution of nucleated cells from erythrocytes. Rather than distinct populations, a continuum of CD45-associated fluorescent events was observed. The consequence of this is contamination of the erythrocyte analyses with leukocytes that failed to exhibit sufficient differential fluorescent resolution. This likely contributed to the high and variable baseline mutation frequencies that were reported by these investigators.

In U.S. Pat. No. 7,824,874 to Dertinger, a method of enumerating Pig-A mutant cell frequency from peripheral blood samples is identified. The described methodology uses a three-color labeling approach to distinguish GPI anchor-deficient cells from GPI anchor-expressing cells, platelets from other blood cells, and reticulocytes from erythrocytes. In U.S. Patent Application Publ. No. US20090311706 to Dertinger and Phonethepswath et al., "Erythrocyte-based Pig-a Gene Mutation Assay: Demonstration of Cross-Species Potential," Mutat. Res. 657:122-126 (2008), another method of enumerating Pig-A mutation frequency from peripheral blood samples is identified. In this method, the peripheral blood sample is treated in a manner to substantially separate RBCs from platelets and leukocytes, thereby enriching the sample for RBCs and making the method less susceptible to spuriously high readings. However, in both cases, the time required to evaluate millions of cells, especially reticulocytes, for the Pig-A mutant phenotype is a very time-consuming process, and most analyses are therefore based on suboptimal numbers of total cells interrogated for the mutant phenotype. This situation leads to less reliable estimates of mutation frequency, especially in situations when mutation frequency is low, as is typically the case in individuals that have not been exposed to potent mutagen(s). It would be desirable to obtain an assay that can identify and quantify many more Pig-A mutant phenotype cells per unit time. Such an assay would be more practical to perform, in terms of efficiently studying large numbers of specimens, and it would be endowed with greater reliability and sensitivity, i.e., greater power to detect modest changes to the frequency of mutant phenotype erythrocytes and/or mutant phenotype reticulocytes.

The present invention is directed to overcoming these and other deficiencies in the prior art.

DEFINITIONS

For purposes of the present invention, the following terms are defined as follows:

"PIG-A" and "Pig-A" are intended to mean the phosphatidylinositol glycan complementation group A gene. When referring to the human gene, the convention is to capitalize all letters, that is, PIG-A. When referring to other species, the convention is to use lower case letters, that is, Pig-a. However, for the purposes of the present invention, the term Pig-A is meant to refer to any vertebrate species, including man.

"GPI" is intended to mean glycosylphosphatidylinositol, a glycolipid that is attached to the C-terminus of certain proteins during posttranslational modification. Certain GPI-anchored proteins such as CD24, CD59 and CD55 normally appear on the cell surface of erythrocytes.

"Erythrocytes" is intended to mean enucleated red blood cells, regardless of RNA content. Erythrocytes is abbreviated RBCs.

"Normochromatic erythrocytes" is intended to mean enucleated red blood cells that have matured to the point that RNA content is negligible. Normochromatic erythrocytes is abbreviated NCEs.

"Reticulocytes" is intended to mean recently formed enucleated red blood cells that are characterized by the presence of cytoplasmic RNA. Reticulocytes is abbreviated RETs.

"Pig-A mutant cells" is intended to mean erythrocytes and/or reticulocytes with altered Pig-A DNA sequence, such that transcription of the Pig-A gene is affected, resulting in a phenotype that is distinguishable by either a lack of or significant deficiency of GPI-anchored proteins on the cell surface.

"Wild-type cells" is intended to mean erythrocytes and/or reticulocytes with a normal complement of GPI-anchored proteins on the cell surface.

"Paramagnetic beads" is intended to mean paramagnetic particles, typically though not exclusively nanoparticles, coated with antibodies or other ligands that bind to a specific surface antigen. This causes the cells expressing this antigen to attach to the paramagnetic beads (or vice versa). Afterwards the cell solution is transferred on a column placed in a strong magnetic field. In this step, the magnetic field should be strong enough such that the cells attached to the paramagnetic beads (expressing the antigen) stay on the column, while other cells (not expressing the antigen) flow through. With this process, the cells can be physically separated based on antigen expression profiles.

"Counting beads" is intended to mean latex particles or other flow cytometry-compatible particles that can be resolved from cells based on light scatter and/or fluorescence emission that are used to generate cell to Counting Bead ratios.

"Expression time" is intended to mean the period of time following exposure of a DNA damaging event until the time that a mutated cell both expresses the GPI-anchor deficient phenotype and also appears in the tissue compartment under consideration (for example, in peripheral blood circulation).

SUMMARY OF THE INVENTION

A first aspect of the present invention relates to methods for the enumeration of Pig-A mutant phenotype cells, especially erythrocytes and reticulocytes.

According to one embodiment, this method includes the steps of: providing an enriched erythrocyte sample obtained from a mammal exposed to an exogenous agent, said sample comprising normochromatic erythrocytes and reticulocytes, and having a reduction in the frequency of platelets and leukocytes; contacting the enriched erythrocyte sample with a first fluorescent reagent that labels GPI anchor-expressing erythrocytes, but not GPI anchor-deficient erythrocytes, and a second fluorescent reagent that specifically labels platelets; separating the enriched erythrocyte sample into a first portion comprising platelets and GPI anchor-expressing erythrocytes and a second portion comprising GPI anchor-deficient erythrocytes; contacting the enriched erythrocyte sample or the second portion with a third fluorescent reagent that differentially labels normochromatic erythrocytes from reticulocytes and leukocytes; exciting the first, second, and third fluorescent reagents in the second portion with light of appropriate excitation wavelength, wherein the third fluorescent reagent has a fluorescent emission spectrum that does not substantially overlap with the fluorescent emission spectra of the first and/or second fluorescent reagents; and detecting the fluorescent emission and light scatter produced by the GPI anchor-deficient erythrocytes of the second portion labeled with the third fluorescent reagent, while excluding contaminating GPI anchor-expressing erythrocytes and reticulocytes, platelets, and leukocytes, and counting the number of GPI anchor-deficient erythrocytes and reticulocytes.

According to another embodiment, this method includes the steps of: providing an enriched erythrocyte sample obtained from a mammal exposed to an exogenous agent, said sample comprising normochromatic erythrocytes and reticulocytes, and having a reduction in the frequency of platelets and leukocytes; contacting the enriched erythrocyte sample with a first fluorescent reagent that labels GPI anchor-expressing erythrocytes, but not GPI anchor-deficient erythrocytes, and a second fluorescent reagent that specifically labels platelets; obtaining a quantitative measure of the total number of erythrocytes and/or reticulocytes in the enriched erythrocyte sample; separating the enriched erythrocyte sample into a first portion comprising platelets and GPI anchor-expressing erythrocytes and a second portion comprising GPI anchor-deficient erythrocytes; contacting the enriched erythrocyte sample or the second portion with a third fluorescent reagent that differentially labels normochromatic erythrocytes from reticulocytes and leukocytes; exciting the first, second, and third fluorescent reagents in the second portion with light of appropriate excitation wavelength, wherein the third fluorescent reagent has a fluorescent emission spectrum that does not substantially overlap with the fluorescent emission spectra of the first and/or second fluorescent reagents; detecting the fluorescent emission and light scatter produced by the GPI anchor-deficient erythrocytes of the second portion labeled with the third fluorescent reagent, while excluding contaminating GPI anchor-expressing erythrocytes and reticulocytes, platelets, and leukocytes, and counting the number of GPI anchor-deficient erythrocytes and reticulocytes; and calculating the frequency of GPI anchor-deficient erythrocytes and/or reticulocytes relative to total erythrocytes and/or reticulocytes present in the sample.

A second aspect of the present invention relates to a method of assessing the DNA-damaging potential of an exogenous chemical or physical agent. This method is carried out by exposing a mammal to an exogenous chemical or physical agent, and then performing the method according to the first aspect of the present invention, wherein a significant deviation in the frequency of mutant phenotype RBCs or RETs from a baseline mutant phenotype RBC or RET frequency in unexposed or vehicle control mammals indicates the genotoxic potential of the exogenous chemical or physical agent.

A third aspect of the present invention relates to a method of evaluating the effects of an exogenous agent that can modify endogenously-induced DNA damage. This method is carried out by administering to a mammal an exogenous agent that may modify endogenously-induced genetic damage; and then performing the flow cytometric method according to the first aspect of the present invention, wherein a significant deviation in the frequency of mutant phenotype RBCs or RETs from a baseline mutant phenotype RBC or RET frequency indicates that the exogenous agent can modify endogenous DNA damage.

A fourth aspect of the present invention relates to a method of evaluating the effects of an exogenous agent that can modify exogenously-induced DNA damage. This method is carried out by administering to a mammal a first exogenous agent that may modify exogenously-induced genetic damage; exposing the mammals to a second exogenous agent that causes genetic damage; and then performing the flow cytometric method according to the first aspect of the present invention, wherein a significant deviation in the frequency of mutant phenotype RBCs or RETs for genotoxicant-exposed mammals indicates that the first exogenous agent can modify exogenously-induced DNA damage.

A fifth aspect of the present invention relates to a kit that can be used to practice the methods of the present invention. The kit preferably includes a first fluorescent reagent that binds GPI anchor-expressing RBCs, but not GPI anchor-deficient RBCs; a second fluorescent reagent that specifically labels platelets, where the second fluorescent reagent has a fluorescent emission spectrum that may or may not substantially overlap with the fluorescent emission spectra of the first fluorescent reagent; a third fluorescent reagent differentiates normochromatic erythrocytes, reticulocytes, and leukocytes; a first product suitable for cell separation; a second product suitable for cell separation; and an instruction manual containing instructions for detecting and calculating the frequency of GPI anchor-deficient erythrocytes and/or reticulocytes relative to total erythrocytes and/or reticulocytes in the sample.

As demonstrated herein, improved methods for enumerating Pig-A mutation frequency in blood specimens are described. The experimental results presented in the accompanying examples were conducted with Sprague Dawley rats. Two peripheral blood erythrocyte populations were evaluated for the GPI anchor-deficient phenotype: RBCs, and the newly formed immature fraction, RETs. As demonstrated by the accompanying examples, the present invention can achieve in vivo mutant cell frequency measurements with previously unattainable precision and rates of data acquisition. Moreover, the experimental results confirm that the invention can be practiced with a variety of genotoxicants that cause genetic damage via different modes.

BRIEF DESCRIPTION OF THE DRAWINGS

FIG. 5A shows the mean percentage of reticulocytes (% RETs) versus time. FIG. 5B shows the mean mutant reticulocyte ($RET^{CD59-}$) frequencies versus time. FIG. 5C shows the mean mutant erythrocyte ($RBC^{CD59-}$) frequencies versus time. Error bars signify standard error of the mean. Asterisks indicate statistical significance compared to same-day vehicle control values (Dunnett's t-test, $p<0.05$; note that analyses were performed on log-transformed data, therefore statistical comparisons were based on log means rather than arithmetic means).

DETAILED DESCRIPTION OF THE INVENTION

The present invention is directed to methods and kits for the measurement of RET frequency, Pig-A mutant phenotype RBC frequency, and Pig-A mutant phenotype RET frequency. These methods and kits can be used with an optical device designed for illumination and analysis of cell specimens.

Preferably, these measurements are accomplished using flow cytometry technology. The advantageous characteristics of this invention relative to other in vivo mutation assays which have been reported to date are that it does not require transgenic animals, special breeding programs, or cell culture; and it is compatible with all mammalian species. Other advantages will become apparent in the discussion of the various embodiments.

With this method, blood specimens are obtained from mammals. If the exposure that one wishes to evaluate is acute, then a period of expression time is allowed to occur before samples are collected into an anticoagulant solution according to standard practices. If the exposure that one wishes to evaluate has been protracted, for instance as occurs for subchronic or chronic toxicity tests, then it will usually not be necessary to allow for additional expression time before blood samples are collected. Alternatively, multiple samples can be collected over a period of time to monitor such long-term exposure.

Figure 1:
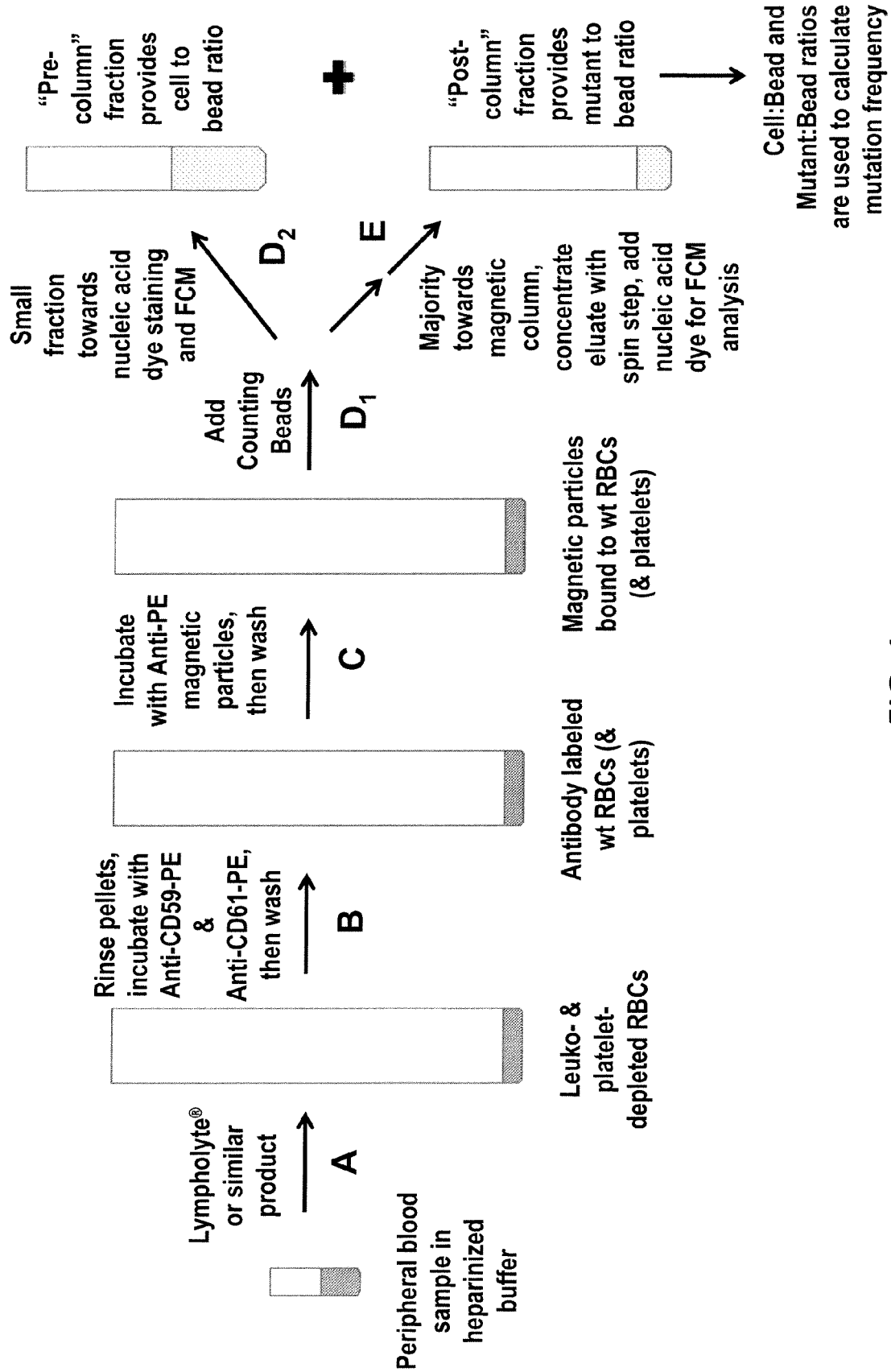
FIG. 1 is a schematic that illustrates the overall strategy used for one embodiment of the present invention to rapidly determine Pig-A mutant cell frequency in peripheral blood samples. Separation of RBCs from leukocytes and platelets of the sample to form an enriched erythrocyte sample can be achieved using Lympholyte®-Mammal or other similar reagent. A phycoerythrin (PE) conjugated anti-CD59 antibody (anti-CD59-PE) represents a preferred first fluorescent reagent for labeling GPI anchor-expressing erythrocytes, but not GPI anchor-deficient erythrocytes, and a PE conjugated anti-CD61 antibody (anti-61-PE) represents a preferred second fluorescent reagent that specifically labels platelets. Anti-PE magnetic particles are preferred reagents for separating the enriched erythrocyte sample into a platelet, GPI anchor-expressing portion and a GPI anchor-deficient portion. The reagents identified in FIG. 1 are exemplary, and the invention is not limited to practice with the reagents illustrated in FIG. 1.

Peripheral blood samples obtained from a subject are preferably treated in a manner effective substantially to separate RBCs from platelets and leukocytes. This is illustrated in FIG. 1, step A. In one embodiment, the sample is enriched for RBCs such that leukocytes and platelets amount to less than about 0.17% of events per sample, more preferably less than about 0.01% of events per sample. One approach for achieving this degree of separation involves separation via centrifugation in an appropriate density gradient, e.g., Lympholyte®-Mammal (Cedarlane Laboratories, Burlington, N.C.), which affords a cell pellet that can be resuspended, e.g., in balanced salt solution, to form an enriched RBC sample. Other commercially available density gradient products that can be used for this purpose exist, for instance Ficoll™ PM400 has a more than 30 year track record for blood cell separation procedures, and is based on a polysucrose and sodium diatrizoate formulation. Additional products include Ficoll-Paque PLUS™, Ficoll-Paque PREMIUM™, Percoll™, and Percoll PLUS™. Whereas some of these products can be purchased at densities that are optimized for use with human blood (i.e., 1.077 g/mL), others have been optimized for mouse and rat blood (1.084 g/mL). Whatever reagent(s) are used for this purpose, the enriched RBC sample can then be treated in the manner described herein.

To achieve Pig-A mutant cell scoring according to the present invention, the enriched RBC sample is incubated with a first fluorescent reagent that binds to GPI-anchor competent (wild-type) RBCs, but not GPI-anchor deficient (Pig-A mutant) RBCs. This is illustrated in FIG. 1, step B. By using a first fluorescent reagent that is either directly conjugated to a fluorochrome, or else one that can be readily bound to a subsequently applied fluorochrome, secondary antibody, or other tag (e.g., biotin), differential labeling of wild-type and mutant phenotype cells can be achieved. Ideally, the specificity of the interaction is high, for instance that which is typically found with antibody-antigen interactions.

Preferred GPI-anchor specific antibodies include, without limitation, fluorochrome-conjugated anti-CD59 and/or anti-CD24 and/or anti-CD55, as well as mixtures thereof. Alternatively, these antibodies can be used in combination with secondary antibodies labeled with a fluorochrome.

Subsequent to or concurrently with differential labeling of mutant phenotype versus wild-type RBCs, the enriched blood sample is contacted with a second fluorescent reagent that specifically binds to platelets (although platelets have largely been eliminated with the reagent used in a previous step to leuko- and platelet-deplete blood samples, some platelets can remain and interfere with analysis). This is also illustrated in FIG. 1 at step B. The second fluorescent reagent can be conjugated directly to a fluorochrome or can be readily bound to a subsequently applied fluorochrome. By using a fluorescent reagent with a different emission spectrum as the first reagent fluorochrome, it is possible to specifically label platelets and thereby exclude them from mutant cell frequency measurements based on this fluorescence signal.

Alternately, it is possible to use the same fluorochrome to label platelets as was used to label wild-type erythrocytes. This one "shared" fluorochrome is appropriate when paramagnetic particles directed against the shared fluorochrome are used to deplete samples of wild-type cells. In this case, platelets are retained along with the wild-type RBCs in the magnetic field and are prevented from interfering with mutant cell scoring. Of the rare platelets that pass through the initial and subsequent physical depletions steps, light scatter is able to provide further differentiation from RBCs. Of the rare platelets that pass through the physical depletions steps as well as light scatter gating criteria, their first fluorochrome-positive phenotype gives them a wild-type RBC characteristic, a situation that does not appreciably effect the rare mutant phenotype RBC or mutant phenotype RET frequency measurements.

Preferred platelet-specific antibodies include, without limitation, anti-CD61 and/or anti-CD42b, as well as mixtures thereof. These antibodies can be directly conjugated to a fluorochrome or can be readily bound to a subsequently applied fluorochrome Subsequent to differential labeling of mutant phenotype versus wild-type RBCs, the enriched blood sample is contacted with a reagent that includes paramagnetic particles and specifically recognizes wild-type RBCs or the fluorochrome, secondary antibody, or other tag associated with the first fluorescent reagent bound to wild-type RBCs. This is illustrated in FIG. 1 at step C. The paramagnetic particles facilitate the separation of the wild-type and mutant RBCs. The paramagnetic particles may also specifically recognize platelets, or the fluorochrome or antibody associated with the second fluorescent reagent bound to the labeled platelets. This facilitates the removal or separation of platelets from the sample.

Figure 3:
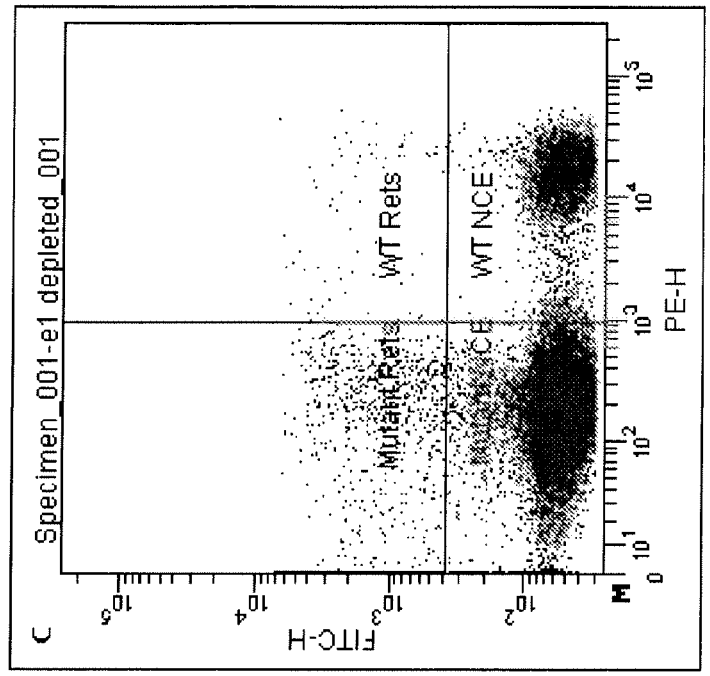
FIG. 3 shows flow cytometric bivariate plots (SYTO®13 fluorescence vs. anti-CD59-PE fluorescence) for a blood specimen from an N-ethyl-N-nitrosourea-treated rat that was processed according to one embodiment of the present invention. The plot to the left shows the results from a pre-magnetic field analysis, whereas the plot to the right shows a post-magnetic field analysis. As shown in the pre-magnetic field analysis (left plot), the wild-type cells (high PE fluorescence signal) vastly outnumber the mutant phenotype cells (low PE fluorescence signal), despite exposure to a potent mutagen. In contrast, as shown in the post-magnetic field analysis (right plot), the wild-type cells are depleted and the mutant phenotype cells (low PE fluorescence signal) are enriched. From these two analyses mutant phenotype RBC and mutant phenotype RET frequencies can be calculated as described herein. The pre-magnetic field analysis is used to determine the total percentage of RETs, the total RBC to counting bead ratio, and the total RET to counting bead ratio. The post-magnetic field analyses are used to determine the mutant phenotype RBC to counting bead ratio and the total mutant phenotype RET to counting bead ratio.
Figure 3:
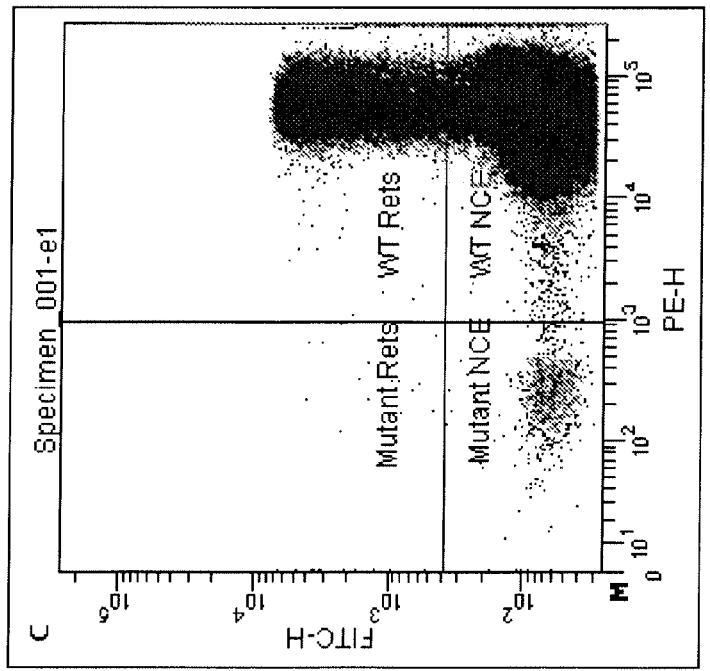

One example of paramagnetic bead-containing reagent includes anti-first fluorochrome beads, for instance Anti-Phycoerythrin (PE) or Anti-Fluorescein (FITC) MicroBeads from Miltenyi Biotec (Germany). FIG. 3 illustrates how effective these particular Anti-PE MicroBeads can be. Here, flow cytometric bivariate plots (SYTO®13 fluorescence vs. anti-CD59-PE fluorescence) are presented for a blood specimen from an N-ethyl-N-nitrosourea-treated rat that was processed according to one embodiment of the present invention. The plot to the left shows the results from a pre-magnetic field analysis, whereas the plot to the right shows a post-magnetic field analysis. As shown in the pre-magnetic field analysis (left plot), wild-type cells (high PE fluorescence signal) ordinarily vastly outnumber mutant phenotype cells (low PE fluorescence signal). In contrast, as shown in the post-magnetic field analysis, the effective use of Anti-PE MicroBeads can severely deplete samples of wild-type cells and thereby greatly enrich samples for mutant phenotype cells (low PE fluorescence signal).

Following sufficient exposure of the enriched sample to the paramagnetic particles, typically on the order of 15 to 30 minutes, the sample is then placed in a magnetic field that is sufficiently strong enough to hold the majority of the wild-type RBCs in the magnetic field while the eluate becomes enriched for mutant phenotype RBCs. This is illustrated in FIG. 1 at step E. This may be accomplished with the aid of a column, for instance one that is packed with ferromagnetic spheres. The eluate, now depleted (or very nearly depleted) of wild-type RBCs and enriched for mutant phenotype RBCs, is then concentrated.

The sample is contacted with a third fluorescent reagent that specifically binds to nucleic acids. This is also illustrated in FIG. 1 at step E. By using a third fluorescent reagent containing a fluorochrome, differential labeling of NCEs, RETs, and any remaining leukocytes is achieved. In one embodiment of the present invention, the concentrated eluate, depleted of wildtype RBCs and enriched for mutant phenotype RBCs is contacted with the third fluorescent reagent that specifically binds to nucleic acids. Exemplary third fluorescent reagents include, without limitation, cyanine dyes, such as those in the SYTO® family of nucleic acid dyes, especially SYTO®13, SYTO®59, SYTO®83, SYTO® RNA Select™ (all available from Invitrogen, USA). Other suitable third fluorescent reagents include thiazole dyes (e.g., thiazole orange) and acridine orange. Of these, SYTO®13 dye is preferred.

In an alternative embodiment of the present invention, the enriched erythrocyte sample is contacted with the third fluorescent reagent prior to separation or enrichment for the mutant RBC phenotype. Exemplary third fluorescent reagents for use in this embodiment of the present invention include reagents that permeate the cells and covalently bind to DNA following photo-induction, e.g., ethidium monoazide (EMA) and propidium monoazide (PMA). In accordance with this embodiment of the present invention, the cells are fixed or otherwise permeabilized using known procedures and reagents prior to exposure to the third fluorescent reagent.

The labeled samples are then subjected to optical detection to enumerate Pig-A mutant cells using any suitable optical detection system. Preferred optical detection systems have one or more light sources, preferably in the form of one or more amplified or collimated beams of light, that are able to excite the fluorescent reagents. Exemplary optical detection systems include, without limitation, single-laser flow cytometers and dual- or multiple-laser flow cytometers.

Single-laser flow cytometric analysis uses a single focused laser beam with an appropriate emission band to excite the several fluorescent reagents. Dual- or multiple-laser flow cytometric analysis use two or more focused laser beams with appropriate emission bands, in much the same manner as a single-laser flow cytometer. Different emission bands afforded by the two or more lasers allow for additional combinations of fluorescent dyes or immunochemical-conjugated fluorochromes to be employed.

As labeled cells pass through the focused laser beam, they exhibit a fluorescent emission maxima characteristic of the fluorochromes or dyes associated therewith. The flow cytometer is equipped with appropriate detection devices to enable detection of the fluorescent emissions and light scatter produced by the cells. In this way, mutant cell populations (i.e., mutant erythrocytes and/or reticulocytes) are counted.

Cell population counts can be expressed as cells per unit volume of sample (i.e., cell density measurement) or per unit time (based on the fluidic rate and the time taken to analyze the sample). Alternatively, counting beads can be added to the sample and the fluorescent emission and light scatter of the counting beads is detected and counted along with the enumerated cell populations to obtain a cell-to-bead ratio. The counting beads can be a suspension of latex particles or similar uniform particle that can be readily differentiated from the cells. Preferred latex particles include, without limitation, CountBright™ Absolute Counting Beads from Invitrogen. In one embodiment of the present invention, such counting beads are added after erythrocytes have been labeled with antibodies and contacted with paramagnetic beads that recognize GPI-anchor-expressing cells. This is schematically illustrated in FIG. 1 at step $D_1$, and FIG. 2. However, it will be appreciated by those knowledgeable in the art that there are alternate and equally acceptable times during the labeling and cell separation procedures when counting beads can be added and used effectively to obtain the desired cell population counts. For instance, in one alternative embodiment of the present invention, counting beads are added to an isotonic buffer solution that includes the third fluorescent reagent used to label nucleic acids. In this case, the dilution factor used to create pre-column samples, and the volume of post-column eluates are important for determining the pre- and post-column cell-to-Counting Bead ratios that are used to calculate mutant cell frequencies.

In order to calculate the frequency of mutant phenotype erythrocytes and/or mutant phenotype reticulocytes relative to total erythrocytes and/or reticulocytes, a quantitative measure of the total number of erythrocytes and reticulocytes in the enriched erythrocyte sample is obtained from the pre-separation sample. This is illustrated in FIG. 1 at step $D_2$. The quantitative measurement can be a cell per volume unit measurement, a cell per unit time measurement, or cell-to-bead ratio as described above. To obtain an accurate frequency calculation, both cell counts (i.e., the mutant phenotype cell counts and the overall total sample cell counts) should be obtained and expressed in the same manner.

While immunodetection reagents are described for use in the methods of the present invention, it should be appreciated that any suitable immunolabel can be used, including without limitation monoclonal antibodies, polyclonal antibodies, mono-specific polyclonal antibody preparations, chimeric antibodies, single chain antibodies, synthetic antibodies, and any antibody fragments, e.g., Fab fragments, Fab' fragments, F(ab)$_2$ fragments, F(ab')$_2$ fragments, Fd fragments, Fv fragments, dAb fragments, and isolated complementarity determining regions ("CDRs") (see U.S. Pat. Nos. 7,037,498, 7,034,121, 7,041,870, and 7,074,405, which are hereby incorporated by reference in their entirety). These antibody fragments can be made by conventional procedures, such as proteolytic fragmentation procedures, as described in J. Goding, *Monoclonal Antibodies: Principles and Practice*, pp. 98-118 (N.Y. Academic Press 1983), which is hereby incorporated by reference in its entirety. Methods for preparing antibodies that are specific to an analyte of interest are well known in the art. Conjugation of desired fluorochromes to antibodies is also well known in the art, and such immunoreagents are commercially available.

Whereas the fluorochrome associated with the first and second fluorescent reagents may be the same, the nucleic acid dye and counting beads, if used, should be selected such that they can all be excited by the one or more light sources, yet their emission spectra are sufficiently distinct.

Samples that have been contacted with three fluorescent reagents as described should be stored at about 4° C. and protected from light until ready for analysis. In a preferred embodiment of the present invention, samples are leuko- and platelet-depleted, stained, and analyzed on the same day of harvest. Alternately, the samples are maintained in a suitable anticoagulant or else leuko- and platelet-depleted, and then stored refrigerated until they can be stained and analyzed, preferably within approximately five days of harvest.

The low frequency of Pig-A mutant cells in healthy mammals, for instance those that are untreated, sham-exposed or vehicle-treated, demands that a sensitive mutation scoring system be capable of interrogating at least several hundred cells per individual, but more ideally greater than $10^6$ cells per individual. Unless considerably more than $10^6$ cells per individual are interrogated per individual, the mutation frequency measurement is a rough approximation, since the spontaneous frequency is thought to be on the order of $1 \times 10^6$. Therefore, to enhance the precision of mutation frequency measurements, especially at or near spontaneous levels, it is important to interrogate many millions of cells for the mutant phenotype. These numbers of cells have been difficult to acquire with current methods, especially for the RET subpopulation of cells. For instance, in Dertinger et al., "Integration of Mutation and Chromosomal Damage Endpoints into 28-Day Repeat Dose Toxicology Studies," *Toxicol. Sci.* 115, 401-411 (2010), which is hereby incorporated by reference in its entirety, the investigators stopped data acquisition once $10^6$ total RBCs were acquired, and in a separate analysis that employed SYTO®13 thresholding, when approximately $0.3 \times 10^6$ RETs were acquired (per sample). These stop modes were dictated by the practical consideration of time spent on the flow cytometer—twenty plus minutes per sample. These stop modes led to a majority of vehicle control analyses returning zero values, a less than ideal situation that diminishes the ability of the assay to detect modest changes to mutation frequency.

While it requires less time to acquire millions of RBCs as opposed to RETs, there are at least two reasons why there is merit in performing Pig-A mutation measurements in the RET fraction in addition to the total RBC pool.

One advantage of RET-based measurements is demonstrated by work with the peripheral blood cells of PNH patients. It has been shown that the number of circulating GPI-deficient neutrophils is typically higher than the number of affected RBCs. One explanation for this finding is that PNH RBCs are subject to complement-mediated intravascular lysis. Therefore, it is possible that an analytical system that focuses on the newly formed RETs would provide a more accurate mutation frequency. At least one previous report supports this view insofar as staining to identify RETs in the blood of PNH patients showed that the percentage of abnormal (GPI-deficient) RETs was similar to the percentage of affected neutrophils (Ware et al., "Immunophenotypic Analysis of Reticulocytes in Paroxysmal Nocturnal Hemoglobinuria," *Blood* 86:1586-1589 (1995), which is hereby incorporated by reference in its entirety). These data indicate that premature destruction of PNH RBCs may account for the fact that most patients have more GPI-deficient neutrophils than RBCs. Thus, a mutation assay based on RETs may be more sensitive than one based on total RBCs, especially if mutant RBCs exhibit a shortened lifespan.

It is important to note, however, that the specimens analyzed by Ware et al. were from PNH patients that expressed high frequencies of mutant RBCs, in the range of approximately 20 to 95%. These high frequencies are not found in non-PNH mammals, even following exposure to potent mutagens. Therefore, Ware et al. were not required to utilize a methodology that was capable of accurately enumerating GPI anchor-deficient cells at baseline and near-baseline frequencies, as is the case for a mutation assay system as described herein.

A second reason for studying Pig-A mutation in RETs is that this subpopulation would be expected to reflect genotoxicant-induced mutation more rapidly than the total RBC pool (Phonethepswath et al., "Pig-a Mutation Kinetics in Rat Erythrocytes Following Exposure to Five Prototypical Mutagens," *Toxicol. Sci.* 114, 59-70 (2010), which is hereby incorporated by reference in its entirety). That is, mutation frequency in the RET population would be expected to be a "leading indicator" of genotoxicant exposure. This temporal relationship reflects the fact that the spontaneous mutant frequency can only be affected by genotoxicant exposure after a sufficient length of time has elapsed, one that allows for a significant fraction of pre-existing (low mutation frequency) cells to be replaced by cells that exhibit an elevated mutation frequency. The time-frame for turning over blood RETs (days) is considerably shorter than for the total RBC pool (several weeks to about 4 months, depending on species), and is consequently expected to provide a quickly responding cohort, versus one that lags in time. Thus, shortening of mutant cell expression time is therefore a major advantage for studying Pig-A mutation in blood RETs.

While rapid interrogation of erythrocytes for the extremely rare Pig-A mutation phenotype is clearly desirable, it is not easily achieved with current methods, especially for the RET subpopulation. In particular, the low incidence of RETs relative to total RBCs poses technical challenges. Despite the high throughput capacity of modern flow cytometers (often on the order of 7000 events per second), the interrogation of approximately $10^6$ RETs for mutation is time consuming. At this rate, a whole blood specimen with 3% RETs would require approximately 80 minutes to interrogate $10^6$ RETs. The invention reported herein overcomes the low throughput capacity of previously described approaches, enabling researchers to interrogate many times more RBCs and RETs than was previously possible, and in a fraction of the time. A second consideration is that data file sizes are extremely large when flow cytometric data for several hundred or more RETs per sample are acquired, and all the mature RBCs that accompany them are also saved to the same data file.

One significant use of the present invention relates to genotoxicity assessment. In this case, an exogenous test agent is applied over a range of doses or intensities to mammals of interest. This test agent exposure may occur one or several times as is the case in acute or subacute toxicity tests, or repeatedly as is the case in subchronic and chronic toxicity tests. The test agent may be a chemical or formulation, or it could be a physical entity, such as energy. Chemicals which are known to damage DNA include, but are not limited to: certain metals (e.g., arsenic, cadmium and nickel), alkylating agents (e.g., N-ethyl-N-nitrosourea, methyl methanesulfonate, etc.), intercalating agents (e.g., proflavin), antimetabolites (e.g., 5-fluorouracil), organic genotoxicants that are generated by combustion processes (e.g., polycyclic aromatic hydrocarbons such as benzo(a)pyrene), as well as organic genotoxicants that are found in nature (e.g., aflatoxins such as aflatoxin B1). Examples of physical agents that are known to damage DNA include, but are not limited to: X-rays, gamma radiation, neutron radiation, beta radiation, and UV radiation.

After an appropriate length of expression time which allows mutated bone marrow stem cells or erythroid progenitor cells to appear in peripheral blood as GPI-anchor deficient RETs or RBCs (i.e., from several days to several weeks post exposure), blood is harvested and prepared for flow cytometric enumeration of Pig-A mutants according to procedures outlined above and described in detail in the following examples.

Certain agents may offer protection from DNA damage, while others may magnify risk of damage. The present invention can also be used to evaluate the effects of an agent which can modify (i.e., enhance or suppress) such damage. To assess the suspected protective effects of an agent, mammals can be exposed to the putative protective agent either prior to, concurrently, or soon after exposure to a known genotoxicant. Any protective effect afforded by the agent can be measured relative to damage caused by the genotoxicant alone. Putative protective agents can be vitamins, bioflavonoids and antioxidants, dietary supplements (e.g., herbal supplements), or any other protective agent, whether naturally occurring or synthesized by man.

To assess the ability of an agent to synergistically or additively enhance genotoxicity, mammals can be exposed to the agent prior to, concurrently, or shortly after exposure to a known genotoxicant. Any additive or synergistic effect caused by the agent can be measured relative to damage caused by the genotoxicant alone.

The assays of the present invention can likewise be used to monitor chronic exposure to genotoxicant agents, for example, in individuals that work in environmental remediation, manufacturing industries that involve exposure to such agents, agricultural environments that involve pesticide or insecticide usage, etc. For these uses, period testing can be performed on a regular basis (e.g., weekly, monthly, quarterly, seasonally, biannually, etc.).

EXAMPLES

The examples below are intended to exemplify the practice of the present invention but are by no means intended to limit the scope thereof.

Example 1

Reproducibility of Technical Replicates

One male Sprague Dawley rat (8-10 weeks old) was treated on three consecutive days (i.e., days 1, 2, and 3) with either vehicle (water) or else 60 mg 1,3-propane sultone (PS) per kilogram body weight per day via oral gavage. Cardiac puncture blood specimens were collected on day 29, that is 26 days after the last administration. Each blood sample was processed (i.e., stained and analyzed via flow cytometry) three separate times to evaluate the reproducibility of cell handling procedures and the analytical platform.

Figure 2:
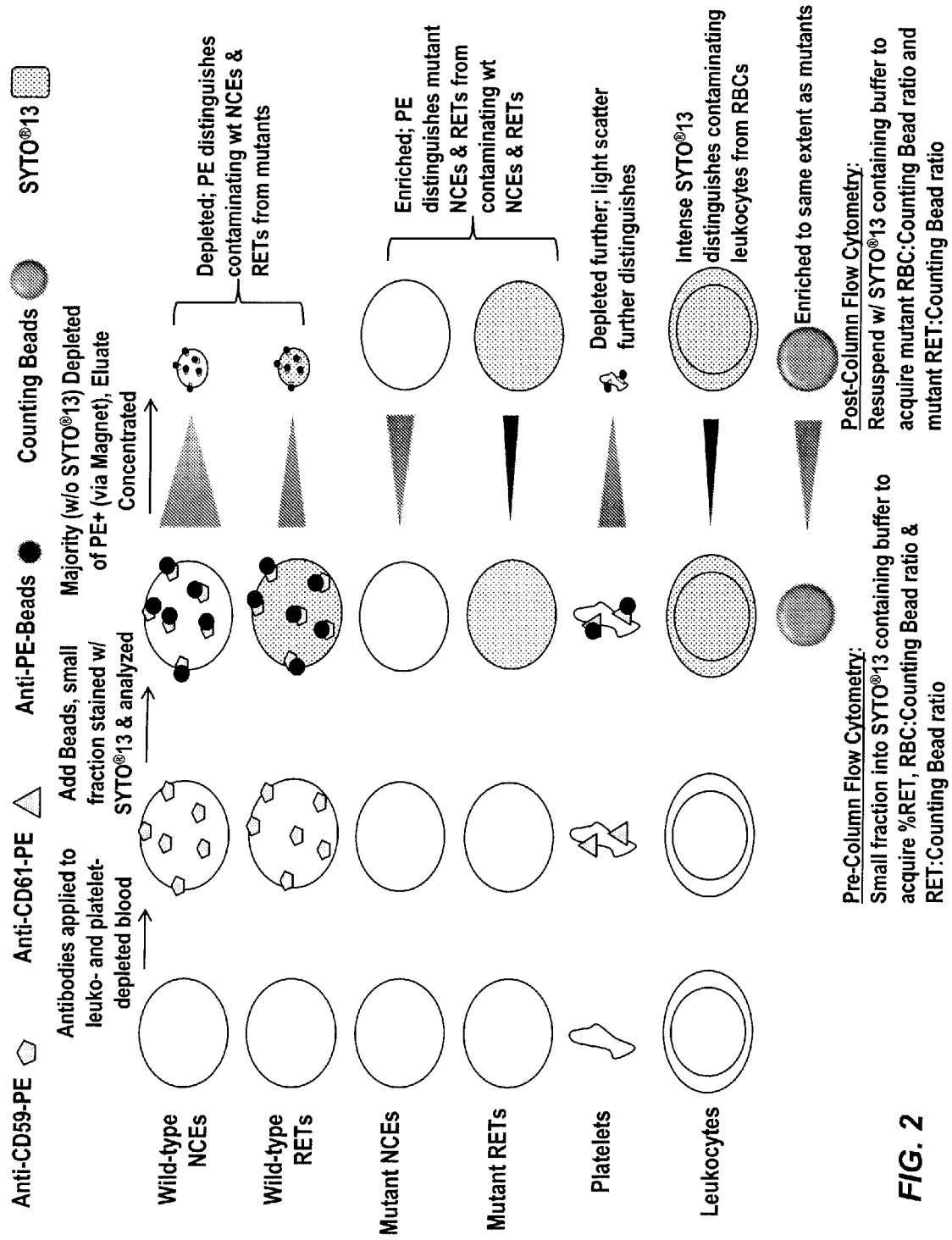
FIG. 2 is a schematic that highlights the differential staining and also the relative depletion/enrichment status for individual cell types with one embodiment of the present invention. As indicated above, anti-CD59-PE and anti-CD61-PE represent preferred first and second fluorescent reagents of the present invention for labeling GPI anchor-expressing erythrocytes and platelets, respectively. Anti-PE magnetic beads are preferred reagents for separating platelets and GPI anchor-expressing erythrocytes from the GPI anchor-deficient erythrocytes, and SYTO®13 represents a preferred third fluorescent reagent for differentially labeling normochromatic erythrocytes from reticulocytes and leukocytes. The reagents identified in FIG. 2 are exemplary, and the invention is not limited to practice with the reagents illustrated in FIG. 2.

FIGS. 1 and 2 illustrate the cell processing procedures used in this study. Specimens of approximately 80 μl whole blood were first debulked of leukocytes and platelets via centrifugation through Lympholyte®-Mammal. Incubation with anti-CD59-PE provided differential labeling of wild-type and mutant phenotype RBCs, while concurrent exposure to anti-CD61-PE endowed rare contaminating platelets with PE fluorescence. Samples were subsequently contacted with Anti-PE MicroBeads from Miltenyi, and after a washing step via centrifugation, latex particles (CountBright™, from Invitrogen) were added in phosphate buffered saline and represented Counting Beads. One fraction of each blood sample was then stained with SYTO®13 and analyzed on a FACS-Canto II flow cytometer running FACS Diva software for 3 minutes each. These "pre-magnetic field" specimens were used to generate the data that appear in Table I, which were used to calculate RBC:Counting Bead and RET:Counting Bead ratios.

After adding Counting Beads to the samples, the majority of each specimen was applied to LC Separation Columns (Miltenyi) that were suspended in a magnetic field (Midi-MACS™ Separator, Miltenyi). 5 mL of phosphate buffered saline was used to elute mutant phenotype cells and Counting Beads, while the column held the vast majority of PE-labeled particles (i.e., wild-type RBCs and contaminating platelets). The eluate was pelleted via centrifugation and resuspended in 300 μl phosphate buffered saline with SYTO®13. These samples were analyzed on the flow cytometer for 4 minutes each. These "post-magnetic field" specimens were used to generate the data that appear in Table II, which were used to calculate mutant phenotype RBC:Counting Bead and mutant phenotype RET:Counting Bead ratios.

Table III shows calculated RET frequencies (percentage) based on the pre-magnetic field analyses, as well as the incidence of mutant phenotype RBCs per $10^6$ RBCs and the incidence of mutant phenotype RETs per $10^6$ RETs that were calculated based on ratios determined in the pre- and post-magnetic field analyses. As these data demonstrate, treatment with the mutagenic chemical PS clearly led to elevated frequencies of mutant phenotype RBCs and RETs, and the results are reproducible across technical replicates.

TABLE I

Flow Cytometric Analyses, Pre-magnetic Field, Technical Replicates

| Treatment (Replicate) | PRE-Magnetic Field Analyses | | | | | | |
|---|---|---|---|---|---|---|---|
| | Mutant RETs | Wt RETs | Mutant NCEs | Wt NCEs | Counting Beads | RBC:Bead Ratio | RET:Bead Ratio |
| Vehicle (1) | 0 | 30,267 | 7 | 1,339,253 | 156 | 8,779.02 | 194.02 |
| Vehicle (2) | 0 | 27,387 | 9 | 1,207,862 | 144 | 8,578.18 | 190.19 |
| Vehicle (3) | 0 | 31,093 | 8 | 1,354,878 | 173 | 8,011.44 | 179.73 |
| PS (1) | 1 | 46,060 | 83 | 1,098,308 | 169 | 6,771.91 | 272.55 |
| PS (2) | 1 | 46,655 | 75 | 1,098,129 | 182 | 6,290.44 | 256.35 |
| PS (3) | 2 | 43,955 | 64 | 1,032,849 | 158 | 6,815.63 | 278.21 |

TABLE II

Flow Cytometric Analyses, Post-magnetic Field, Technical Replicates

POST-Magnetic Field Analyses

| Treatment (Replicate) | Mutant RETs | Mutant NCEs | Counting Beads | Mutant RBC:Bead Ratio | Mutant RET:Bead Ratio | Total RBC Equivalents | Total RET Equivalents |
|---|---|---|---|---|---|---|---|
| Vehicle (1) | 1 | 84 | 16,106 | 0.00528 | 0.00006 | 141,394,884 | 3,124,874 |
| Vehicle (2) | 1 | 81 | 16,681 | 0.00492 | 0.00006 | 143,092,630 | 3,172,518 |
| Vehicle (3) | 1 | 92 | 12,803 | 0.00726 | 0.00008 | 102,570,457 | 2,301,062 |
| PS (1) | 95 | 6,466 | 15,856 | 0.41379 | 0.00599 | 107,375,331 | 4,321,557 |
| PS (2) | 79 | 7,590 | 18,558 | 0.41324 | 0.00426 | 116,737,977 | 4,757,374 |
| PS (3) | 94 | 7,054 | 19,070 | 0.41324 | 0.37483 | 129,974,120 | 5,305,443 |

TABLE III

Calculated Frequencies Derived From Pre- and Post-Magnetic Field Analyses, Technical Replicates Calculated Frequencies

| Treatment (Replicate) | % RET | Mutant RBCs per $10^6$ Total RBCs | Mutant RETs per $10^6$ Total RETs |
|---|---|---|---|
| Vehicle (1) | 2.21 | 0.6 | 0.3 |
| Vehicle (2) | 2.22 | 0.6 | 0.3 |
| Vehicle (3) | 2.24 | 0.9 | 0.4 |
| PS (1) | 4.02 | 61.1 | 22 |
| PS (2) | 4.08 | 65.7 | 16.6 |
| PS (3) | 4.08 | 55 | 17.7 |

Example 2

Spiking Experiment

One male Sprague Dawley rat (7-8 weeks old) was treated on fourteen consecutive days (i.e., days 1-14) with either vehicle (water) or 40 mg 1,3-propane sultone (1,3-PS) per kilogram body weight per day via oral gavage. Cardiac puncture blood specimens were collected on day 35 (i.e., 21 days after the last administration). The blood sample from the vehicle control rat was processed (i.e., stained and analyzed via flow cytometry) two separate times and is referred to herein as the "0" sample; blood from the 1,3-PS-treated rat was processed two separate times and is referred to herein as the "100" sample. To construct a specimen with an intermediate frequency of mutant cells, eight parts vehicle control blood were combined with two parts 1,3-PS blood and this spiked sample (referred to herein as the "20" sample) was processed two separate times. Another intermediate frequency specimen was prepared by combining nine parts vehicle control blood with one part 1,3-PS blood and this spiked sample (referred to herein as the "10" sample) was processed two separate times.

The eight specimens described above were processed as follows: 80 μA whole blood were first debulked of leukocytes and platelets via centrifugation through Lympholyte®-Mammal. Incubation with anti-CD59-PE provided differential labeling of wild-type and mutant phenotype RBCs, while concurrent exposure to anti-CD61-PE endowed rare contaminating platelets with PE fluorescence. Samples were subsequently contacted with anti-PE MicroBeads from Miltenyi, and after a washing step via centrifugation, latex particles (CountBright™, from Invitrogen) were added in phosphate buffered saline and represented Counting Beads. One fraction of each blood sample was then stained with SYTO®13 and analyzed on a FACSCanto II flow cytometer running FACS Diva software for 3 minutes each. These pre-magnetic field specimens were used to generate the data that appear in Table IV, which were used to calculate RBC:Counting Bead and RET:Counting Bead ratios.

After adding Counting Beads to the samples, the majority of each specimen was applied to LC Separation Columns (Miltenyi) that were suspended in a magnetic field (Midi-MACS™ Separator, Miltenyi). 5 mL of phosphate buffered saline was used to elute mutant phenotype cells and Counting Beads, while the column held the vast majority of PE-labeled particles (i.e., wild-type RBCs and contaminating platelets). The eluate was pelleted via centrifugation and resuspended in 300 μl phosphate buffered saline with SYTO®13. These samples were analyzed on the flow cytometer for 4 minutes each. These post-magnetic field specimens were used to generate the data that appear in Table V, which were used to calculate mutant phenotype RBC:Counting Bead and mutant phenotype RET:Counting Bead ratios.

Table VI shows calculated RET frequencies (percentage) based on the pre-magnetic field analyses, as well as the incidence of mutant phenotype RBCs per $10^6$ RBCs and the incidence of mutant phenotype RETs per $10^6$ RETs that were calculated based on ratios determined in the pre- and post-magnetic field analyses.

Figure 4:
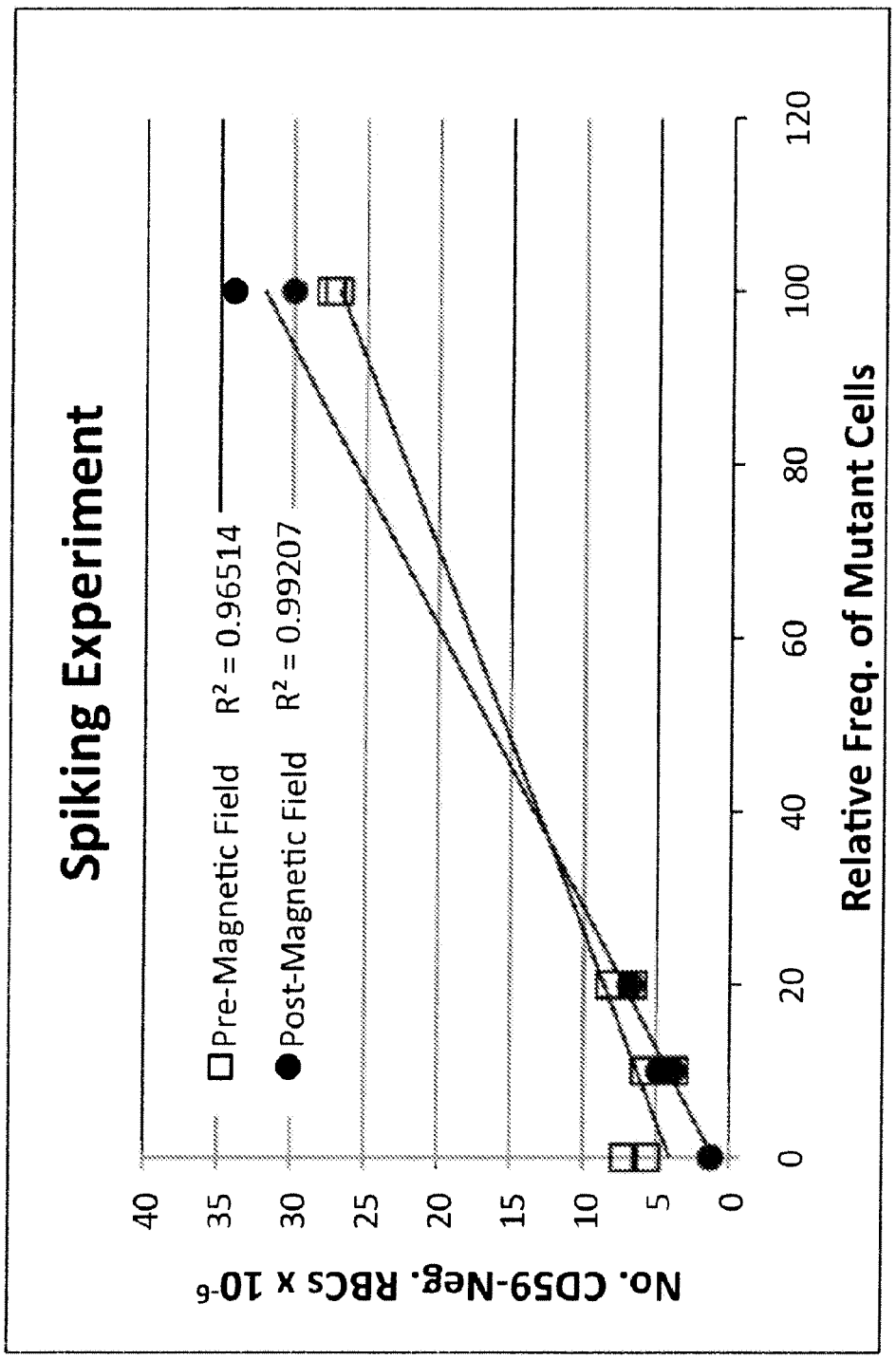
FIG. 4 shows observed mutant phenotype cell frequencies ($\times 10^{-6}$) versus known, relative mutant cell frequencies. Data points depicted by squares represent pre-magnetic field analyses (on average 1,323,693 RBCs interrogated per sample). Data points depicted by circles represent post-magnetic field analyses (on average 112,632,575 RBCs interrogated per sample). The $R^2$ values are linear correlation coefficients.

Table VII shows mutant phenotype RBCs frequencies (per $10^6$ RBCs) based on pre-magnetic field analyses as well as post-magnetic field analyses. Whereas the pre-magnetic field frequency determinations are based on an average of 1,323,693 RBCs per specimen, the post-magnetic field frequency measurements are based on an average of 112,632,575 RBCs per specimen. FIG. 4 is a graph that depicts each observed mutant phenotype cell frequency against the known, relative mutant cell frequency. From these data it is clear that the invention described herein, which includes wild-type cell depletion steps, provides more precise enumeration of rare GPI-anchor deficient cells relative to analyses based on total erythrocytes that do not benefit from depletion step(s).

TABLE IV

Flow Cytometric Analyses, Pre-magnetic Field, Spiking Experiment

PRE-Magnetic Field Analyses

| Sample ID (Replicate) | Mutant RETs | Wt RETs | Mutant NCEs | Wt NCEs | Counting Beads | RBC:Bead Ratio | RET:Bead Ratio |
|---|---|---|---|---|---|---|---|
| 0 (1) | 0 | 37,666 | 7 | 1,206,954 | 186 | 6,691.54 | 202.51 |
| 0 (2) | 0 | 42,322 | 10 | 1,356,514 | 193 | 7,247.91 | 219.28 |

TABLE IV-continued

Flow Cytometric Analyses, Pre-magnetic Field, Spiking Experiment

PRE-Magnetic Field Analyses

| Sample ID (Replicate) | Mutant RETs | Wt RETs | Mutant NCEs | Wt NCEs | Counting Beads | RBC:Bead Ratio | RET:Bead Ratio |
|---|---|---|---|---|---|---|---|
| 10 (1)  | 0 | 45,106 | 5  | 1,290,058 | 151 | 8,842.18 | 298.72 |
| 10 (2)  | 0 | 44,928 | 8  | 1,336,885 | 182 | 7,592.42 | 246.86 |
| 20 (1)  | 0 | 47,520 | 11 | 1,292,199 | 151 | 8,872.38 | 314.70 |
| 20 (2)  | 0 | 48,649 | 9  | 1,308,497 | 159 | 8,535.57 | 305.97 |
| 100 (1) | 1 | 79,656 | 36 | 1,265,814 | 168 | 8,008.97 | 474.15 |
| 100 (2) | 1 | 70,002 | 31 | 1,116,652 | 162 | 7,325.22 | 432.12 |

TABLE V

Flow Cytometric Analyses, Post-magnetic Field, Spiking Experiment

POST-Magnetic Field Analyses

| Treatment (Replicate) | Mutant RETs | Mutant NCEs | Counting Beads | Mutant RBC:Bead Ratio | Mutant RET:Bead Ratio | Total RBC Equivalents | Total RET Equivalents |
|---|---|---|---|---|---|---|---|
| 0 (1)   | 2   | 130   | 16,503 | 0.00800 | 0.00012 | 110,430,534 | 3,341,946 |
| 0 (2)   | 0   | 150   | 16,041 | 0.00935 | 0.00000 | 116,263,672 | 3,517,550 |
| 10 (1)  | 20  | 449   | 13,819 | 0.03394 | 0.00145 | 122,190,069 | 4,127,946 |
| 10 (2)  | 18  | 502   | 13,998 | 0.03715 | 0.00129 | 106,278,738 | 3,455,506 |
| 20 (1)  | 50  | 720   | 13,036 | 0.05907 | 0.00384 | 115,660,399 | 4,102,455 |
| 20 (2)  | 35  | 765   | 13,509 | 0.05922 | 0.00259 | 115,306,962 | 4,133,329 |
| 100 (1) | 173 | 3,304 | 14,475 | 0.24021 | 0.01195 | 115,929,844 | 6,863,304 |
| 100 (2) | 182 | 3,192 | 13,515 | 0.24965 | 0.01347 | 99,000,378  | 5,840,065 |

TABLE VI

Calculated Frequencies Derived From Pre- and Post-Magnetic Field Analyses, Spiking Experiment Calculated Frequencies

| Treatment (Replicate) | % RET | Mutant RBCs per $10^6$ Total RBCs | Mutant RETs per $10^6$ Total RETs |
|---|---|---|---|
| 0 (1)   | 3.03 | 1.2  | 0.6  |
| 0 (2)   | 3.03 | 1.3  | 0    |
| 10 (1)  | 3.38 | 3.8  | 4.8  |
| 10 (2)  | 3.25 | 4.9  | 5.2  |
| 20 (1)  | 3.55 | 6.7  | 12.2 |
| 20 (2)  | 3.58 | 6.9  | 8.5  |
| 100 (1) | 5.92 | 30   | 25.2 |
| 100 (2) | 5.9  | 34.1 | 31.2 |

TABLE VII

Calculated Frequencies, Pre-versus Post-Magnetic Field Analyses, Spiking Experiment Calculated Frequencies

| Treatment (Replicate) | Mutant RBCs per $10^6$ Total RBCs (Pre-Column)* | Mutant RBCs per $10^6$ Total RBCs (Post-Column)** |
|---|---|---|
| 0 (1)   | 6  | 1.2  |
| 0 (2)   | 7  | 1.3  |
| 10 (1)  | 4  | 3.8  |
| 10 (2)  | 6  | 4.9  |
| 20 (1)  | 8  | 6.7  |
| 20 (2)  | 7  | 6.9  |
| 100 (1) | 27 | 30   |
| 100 (2) | 27 | 34.1 |

*Avg. number of RBCs interrogated per sample = 1,323,693
**Avg. number of RBCs interrogated per sample = 112,632,575

Example 3

In Vivo Responses to the Mutagenic Chemical 1,3-Propane Sultone

Groups consisting of six male Sprague Dawley rats (7-8 weeks old) were treated on twenty-eight consecutive days (i.e., days 1 through 28) with either water (vehicle), 12.5 mg 1,3-PS per kilogram body weight per day, 25 mg 1,3-PS per kilogram body weight per day, or 50 mg 1,3-PS per kilogram body weight per day via oral gavage. Note that one rat in the high dose group died on day 11 and others in this group continued to lose weight, therefore after 14 days of administering 50 mg/kg/day, the top dose was reduced to 37.5 mg/kg/day for the remaining 14 days of administration. Tail vein blood specimens were collected on day −1 (i.e., one day before the start of treatment), and again on days 15, 29, and 42.

Each blood sample was processed according to procedures outlined in FIGS. 1 and 2. More specifically, specimens consisting of 80 μl whole blood each were first debulked of leukocytes and platelets via centrifugation through Lympholyte®-Mammal. Incubation with anti-CD59-PE provided differential labeling of wild-type and mutant phenotype RBCs, while concurrent exposure to anti-CD61-PE endowed rare contaminating platelets with PE fluorescence. Cells were subsequently contacted with Anti-PE MicroBeads from Miltenyi, and after a washing step via centrifugation, latex particles (CountBright™, from Invitrogen) were added in phosphate buffered saline and represented Counting Beads. One fraction of each blood sample was then stained with SYTO®13 and analyzed on a FACSCalibur flow cytometer running CellQuest Pro software for 3 minutes each. These pre-magnetic field specimens were used to generate the data used to calculate RBC:Counting Bead and RET:Counting Bead ratios.

After adding Counting Beads to the samples, the majority of each specimen was applied to LC Separation Columns (Miltenyi) that were suspended in a magnetic field (QuadroMACS™ Separator, Miltenyi). 5 mL of phosphate buffered saline was used to elute mutant phenotype cells and Counting Beads, while the column held the vast majority of PE-labeled particles (i.e., wild-type RBCs and contaminating platelets). The eluate was pelleted via centrifugation and resuspended in 300 µl phosphate buffered saline with SYTO®13. These samples were analyzed on the flow cytometer for 3-3.5 minutes each. These post-magnetic field specimens were used to generate the data used to calculate mutant phenotype RBC:Counting Bead and mutant phenotype RET:Counting Bead ratios.

Figure 5A:
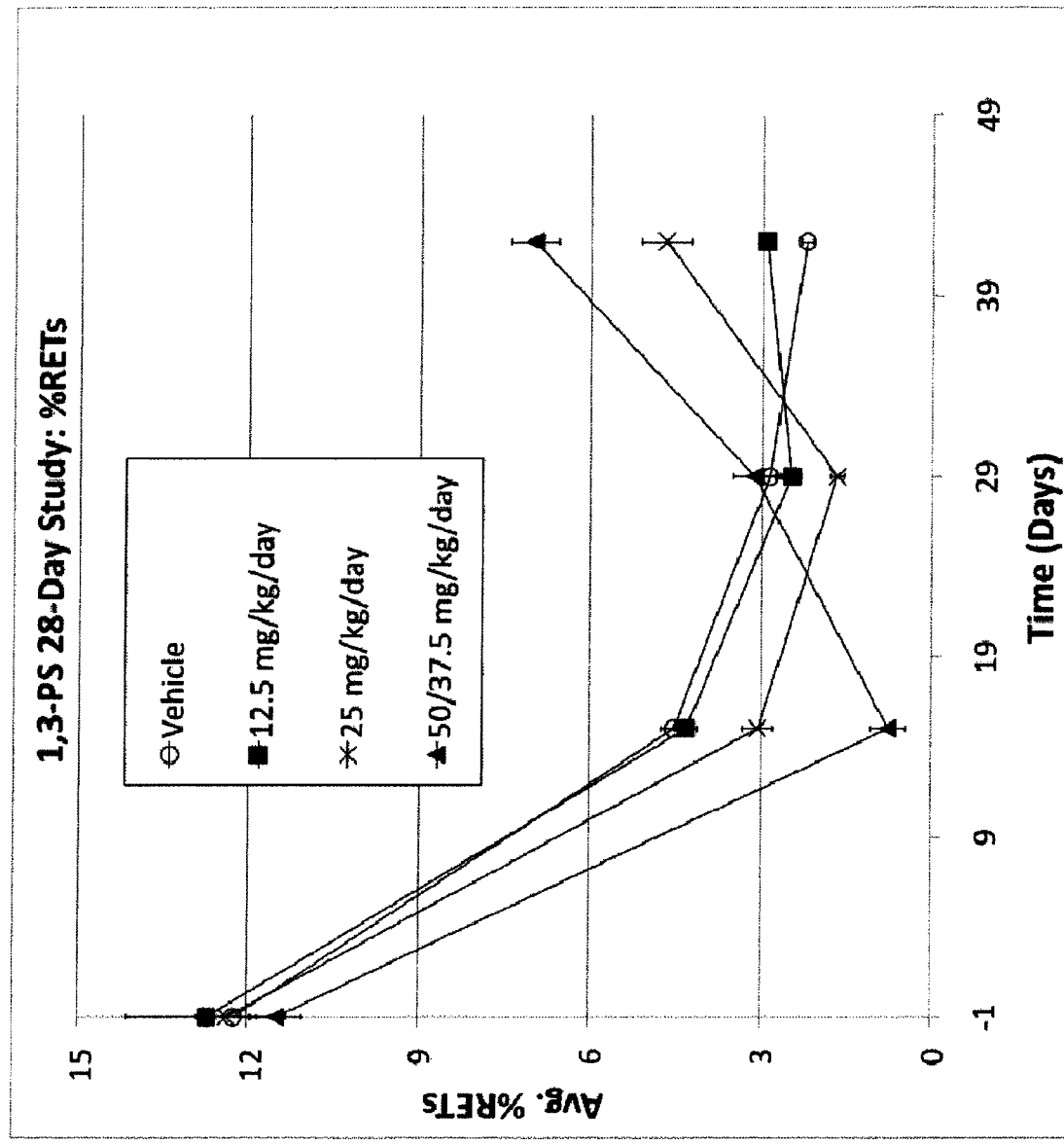
FIGS. 5A-5C show longitudinal data from a 28-day 1,3-propane sultone (1,3-PS) study.

Longitudinal % RET data are shown in FIG. 5A. Day 15% RET were reduced in a dose-dependent manner, and a rebound effect was evident at the top two dose levels at later time points with % RET increasing and ultimately exceeding vehicle control values.

Figure 5B:
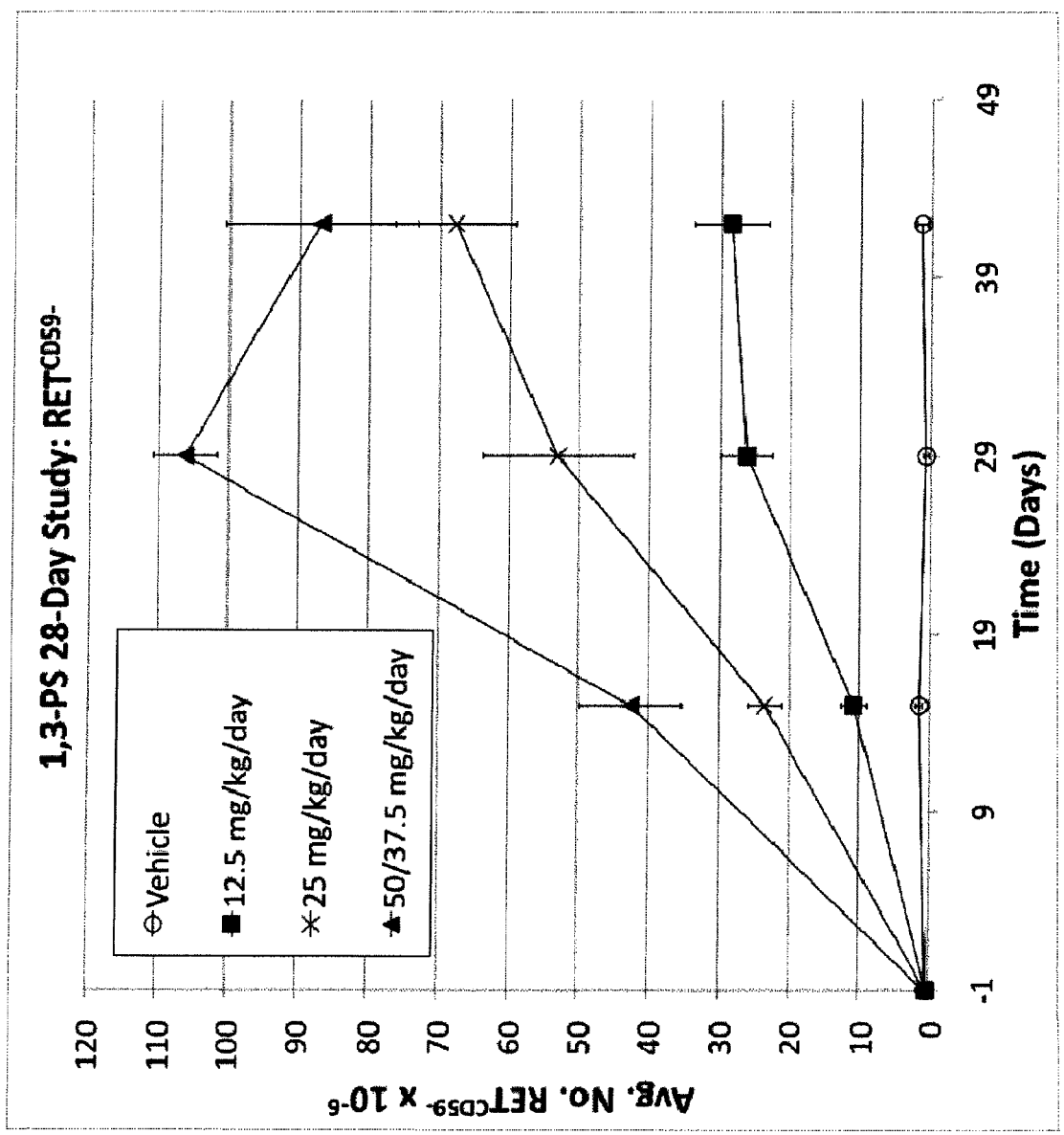

As shown by FIG. 5B, elevated mutant phenotype cells were first observed in the RET population. These increases occurred in a dose-dependent manner, and each dose group was significantly elevated relative to vehicle controls at every time point studied. While a modest reduction to the top dose group's mean mutant RET frequency was observed between days 29 and 42, the other dose groups exhibited similar or slightly elevated values over this same timeframe.

Figure 5C:
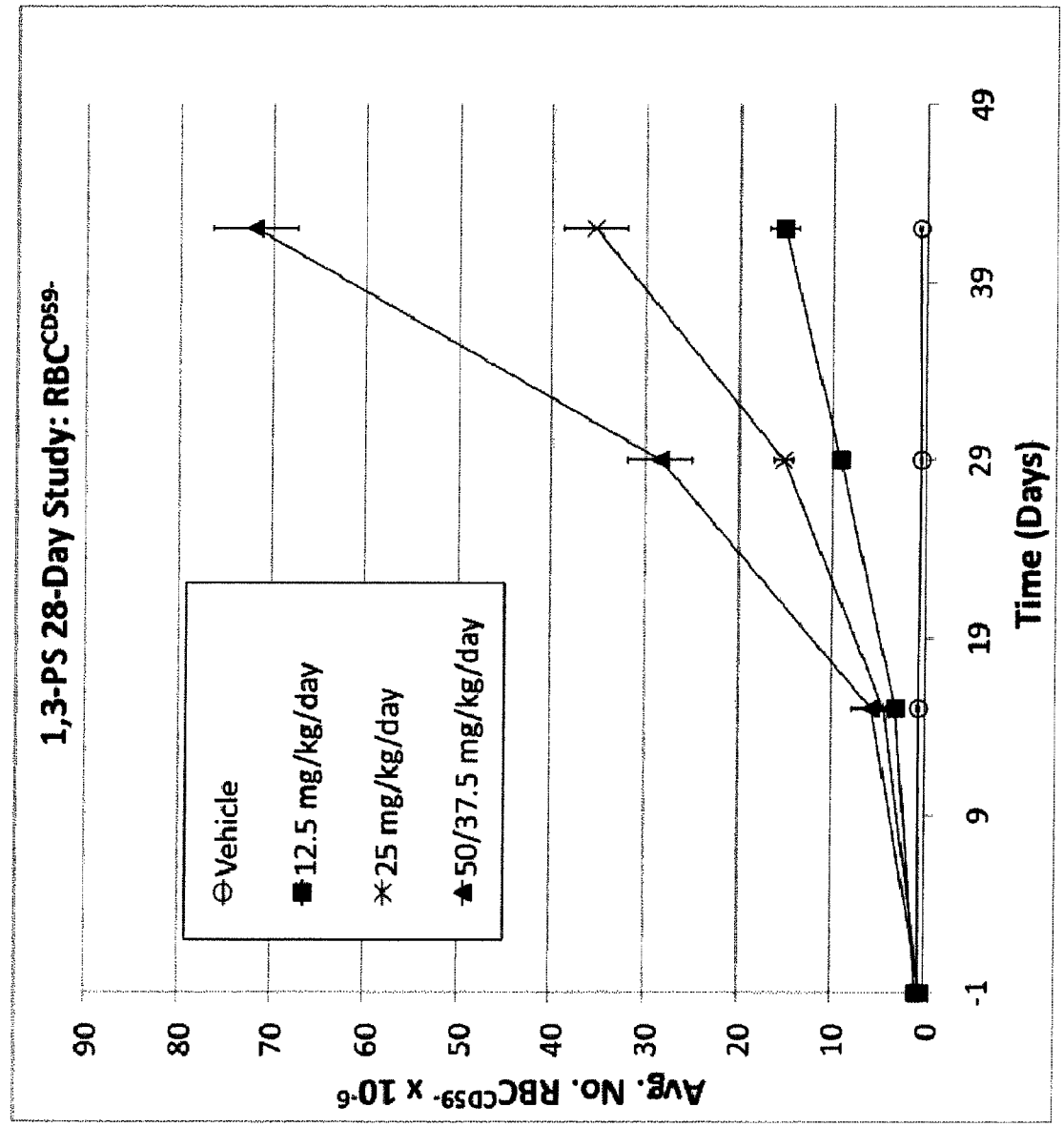

Mutant RBC frequencies increased at a slower rate compared to mutant RETs, with maximal observed values occurring on day 42 (FIG. 5C). Each of the 1,3-PS dose groups exhibited elevated frequencies that were significantly higher than those observed in vehicle-treated rats from Day 15 through Day 42, even at Day 15 where the increases over the baseline were relatively small.

The immunomagnetic separation procedure proved capable of analyzing large numbers of RETs and RBCs for the mutant phenotype. For example, considering the day 29 time point, the average number of cell equivalents interrogated for CD59 expression was $1.18 \times 10^8$ RBCs and $2.93 \times 10^6$ RETs per sample. As these values are on the order of 100× and 10× higher than previous work with these endpoints (Phonethepswath et al., "Pig-a Mutation: Kinetics in Rat Erythrocytes Following Exposure to Five Prototypical Mutagens," *Toxicol. Sci.* 114:59-70 (2010); Dertinger et al., "Integration of Mutation and Chromosomal Damage Endpoints into 28-Day Repeat Dose Toxicology Studies," *Toxicol. Sci.* 115: 401-411 (2010), each of which is hereby incorporated by reference in its entirety), it was of interest to evaluate the statistical power of this new methodology. As shown in Table VIII, given a group size of 6 rats, 3-fold increases in mutant RETs and 2-fold increases in mutant RBCs were detectable with greater than 80% power.

TABLE VIII

Power Analyses, Based on Day 29 Data

| Parameter | Increase Over Baseline | Chance of Detecting |
| --- | --- | --- |
| Mutant RETs | 2x | 49% |
| | 2.5x | 69% |
| | 3x | 82% |
| | 3.5x | 90% |
| | 4x | 95% |
| Mutant RBCs | 2x | 90% |
| | 2.5x | 99% |
| | 3x | 99.9% |
| | 3.5x | >99.9% |
| | 4x | >99.9% |

Example 4

In Vivo Responses to Diverse Mutagenic Chemicals

The same experimental design used in Example 3 was used to study several additional mutagenic chemicals agents. That is, groups of six male Sprague Dawley rats (age 7-8 weeks) were treated for twenty-eight consecutive days with vehicle, low, mid, and high dose levels of each test article via oral gavage. High dose levels approximated maximum tolerated doses, mid dose was one-half of the high dose, and low dose was one-quarter of the high dose. The identity of these chemicals and their primary mode of action are presented in Table IX.

Tail vein blood samples were collected from each animal over time, specifically on day −1 (i.e., one day before the start of treatment), and again on days 15, 29, and 42. Each blood sample was processed according to procedures outlined in FIGS. 1 and 2. More specifically, specimens consisting of 80 µl whole blood each were first debulked of leukocytes and platelets via centrifugation through Lympholyte®-Mammal. Incubation with anti-CD59-PE provided differential labeling of wild-type and mutant phenotype RBCs, while concurrent exposure to anti-CD61-PE endowed rare contaminating platelets with PE fluorescence. Cells were subsequently contacted with Anti-PE MicroBeads from Miltenyi, and after a washing step via centrifugation, latex particles (CountBright™, from Invitrogen) were added in phosphate buffered saline and represented Counting Beads. One fraction of each blood sample was then stained with SYTO®13 and analyzed on a FACSCalibur flow cytometer running CellQuest Pro software for 3 minutes each. These pre-magnetic field specimens were used to generate the data used to calculate RBC:Counting Bead and RET:Counting Bead ratios.

After adding Counting Beads to the samples, the majority of each specimen was applied to LC Separation Columns (Miltenyi) that were suspended in a magnetic field (QuadroMACS™ Separator, Miltenyi). Five milliliters of phosphate buffered saline was used to elute mutant phenotype cells and Counting Beads, while the column held the vast majority of PE-labeled particles (i.e., wild-type RBCs and contaminating platelets). The eluate was pelleted via centrifugation and resuspended in 300 µl phosphate buffered saline with SYTO®13. These samples were analyzed on the flow cytometer for 3-3.5 minutes each. These post-magnetic field specimens were used to generate the data used to calculate mutant phenotype RBC:Counting Bead and mutant phenotype RET:Counting Bead ratios.

Each of these diverse genotoxic chemicals was observed to significantly increase the frequency of circulating mutant RETs and RBCs. The data are summarized in Table IX, which provides information about the time point at which the maximal effect was observed for both the mutant RET and mutant RBC endpoints.

TABLE IX

Maximum Mutant Cell Responses for a Series of Diverse Genotoxicants

| Chemical | Mode of Genotoxic Action | Maximum Avg. Mutant Cell Freq. × $10^{-6}$ (Day Maximum Value was Observed) |
| --- | --- | --- |
| Thiotepa | Alkylating agent, organophosphorus compound | 79 Mutant RETs (d29); 69 Mutant RBCs (d42) |

TABLE IX-continued

Maximum Mutant Cell Responses for a Series of Diverse Genotoxicants

| Chemical | Mode of Genotoxic Action | Maximum Avg. Mutant Cell Freq. × $10^{-6}$ (Day Maximum Value was Observed) |
|---|---|---|
| 2-Acetylaminofluorene | Aromatic amine | 50 Mutant RETs (d42); 58 Mutant RBCs (d29) |
| Chlorambucil | Alkylating agent, nitrogen mustard | 40 Mutant RETs (d42); 21 Mutant RBCs (d42) |
| Melphalan | Alkylating agent, nitrogen mustard | 33 Mutant RETs (d42); 23 Mutant RBCs (d42) |
| Cyclophosphamide | Alkylating agent, nitrogen mustard | 5 Mutant RETs (d29); 3 Mutant RBCs (d42) |
| Azathioprine | Purine analog | 13 Mutant RETs (d29); 4 Mutant RBCs (d42) |
| 1,3-Propane Sultone (see Example 3 above) | Alkylating agent, cyclic sulfonate ester | 106 Mutant RETs (d29); 72 Mutant RBCs (d42) |

Note that untreated male Sprague Dawley rats' historical control mean mutant RET and mutant RBC frequencies are < 1 × $10^{-6}$.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of assessing mutagenic DNA-damaging potential of an agent, the method comprising:
   A. providing an enriched erythrocyte sample obtained from a mammal exposed to an agent that may induce mutagenic DNA damage, said sample comprising normochromatic erythrocytes and reticulocytes, and having a reduction in the frequency of platelets and leukocytes;
   B. contacting the enriched erythrocyte sample with a first fluorescent reagent that labels glycosylphosphatidylinositol (GPI) anchor-expressing erythrocytes, but not GPI anchor-deficient erythrocytes, and a second fluorescent reagent that specifically labels platelets;
   C. contacting the enriched erythrocyte sample with paramagnetic particles that bind specifically to the first fluorescent reagent of the labeled GPI anchor-expressing erythrocytes and, optionally, the second fluorescent reagent of the labeled platelets;
   D. magnetically separating the enriched erythrocyte sample into a first portion comprising platelets and GPI anchor-expressing erythrocytes and a second portion comprising GPI anchor-deficient erythrocytes;
   E. contacting the enriched erythrocyte sample or the second portion with a third fluorescent reagent that differentially labels normochromatic erythrocytes from reticulocytes and leukocytes;
   F. exciting the first, second, and third fluorescent reagents in the second portion with light of appropriate excitation wavelength, wherein the third fluorescent reagent has a fluorescent emission spectrum that does not substantially overlap with the fluorescent emission spectra of the first or second fluorescent reagents; and
   G. detecting the fluorescent emission and light scatter produced by the GPI anchor-deficient erythrocytes of the second portion labeled with the third fluorescent reagent, while excluding contaminating GPI anchor-expressing erythrocytes and reticulocytes, platelets, and leukocytes, and counting the number of GPI anchor-deficient erythrocytes and reticulocytes relative to the total number of erythrocytes and reticulocytes, respectively, in the enriched erythrocyte sample, wherein a statistically significant deviation in the frequency of GPI anchor-deficient erythrocytes or reticulocytes from a baseline frequency of GPI anchor-deficient erythrocytes or reticulocytes in a sample from an unexposed or vehicle control exposed mammal indicates the mutagenic DNA-damaging potential of the agent.

2. The method according to claim 1, wherein the first fluorescent reagent comprises an anti-CD59, anti-CD24, or anti-CD55 antibody, or a combination thereof.

3. The method according to claim 1, wherein the second fluorescent reagent comprises an anti-CD61 antibody or anti-CD42b antibody, or a combination thereof.

4. The method according to claim 1, wherein the third fluorescent reagent is a nucleic acid dye.

5. The method according to claim 4, wherein the nucleic acid dye is a cyanine dye or a thiazole dye.

6. The method according to claim 4, wherein said contacting in step E is carried out on the second portion.

7. The method according to claim 4, wherein the nucleic acid dye covalently binds nucleic acids.

8. The method according to claim 7, wherein said method further comprising permeabilizing cells in the enriched erythrocyte sample prior to said contacting in step E.

9. The method according to claim 1, wherein said magnetically separating comprises:
   subjecting the enriched erythrocyte sample containing the paramagnetic particles to a magnetic field under conditions effective to retain the labeled GPI anchor-expressing erythrocytes, but not GPI anchor-deficient erythrocytes in the magnetic field; and
   collecting the GPI anchor-deficient erythrocytes not retained in the magnetic field to obtain the second portion.

10. The method according to claim 9 further comprising concentrating the collected GPI anchor-deficient erythrocytes.

11. The method according to claim 9, wherein the paramagnetic particles also bind to the second fluorescent reagent-labeled platelets, and said subjecting retains labeled platelets in the magnetic field.

12. The method according to claim 1, wherein the paramagnetic particles are anti-Phycoerythrin (PE) or anti-FITC beads.

13. The method according to claim 1 further comprising:
   obtaining a quantitative measure of the total number of erythrocytes and/or reticulocytes in the enriched erythrocyte sample; and
   calculating the frequency of GPI anchor-deficient erythrocytes and/or reticulocytes relative to total erythrocytes and/or reticulocytes present in the sample.

14. The method according to claim 13, wherein said obtaining comprises:
   contacting the enriched erythrocyte sample with a fluorescent reagent that differentially labels normochromatic erythrocytes from reticulocytes and leukocytes;
   exciting the fluorescent reagent with light of appropriate excitation wavelength;

detecting the fluorescent emission and light scatter produced by the fluorescent reagent, and counting the number of erythrocytes and/or reticulocytes per unit volume of sample.

15. The method according to claim 13, further comprising:
adding counting beads to the enriched erythrocyte sample prior to said separating or to the second portion after said separating;
counting, during said detecting step, the number of counting beads; and
calculating a GPI anchor-deficient erythrocyte to bead ratio and/or GPI anchor-deficient reticulocyte to bead ratio.

16. The method according to claim 15, wherein said obtaining comprises:
contacting the enriched erythrocyte sample containing counting beads with a fluorescent reagent that differentially labels normochromatic erythrocytes from reticulocytes and leukocytes;
exciting the fluorescent reagent and counting beads with light of appropriate excitation wavelength;
detecting the fluorescent emission and light scatter produced by the fluorescent reagent and counting beads, and counting the number of erythrocytes and/or reticulocytes and counting beads in the sample; and
calculating an erythrocyte to bead ratio and/or reticulocyte to bead ratio.

17. The method according to claim 15, wherein the counting beads are fluorescent latex microspheres.

18. The method according to claim 1, wherein said exciting is carried out with a single-laser or multiple-laser flow cytometer.

19. A method of evaluating the effects of an agent that may modify mutagenic DNA damage comprising:
providing an enriched erythrocyte sample obtained from a mammal exposed to an agent that may modify mutagenic DNA damage, said sample comprising normochromatic erythrocytes and reticulocytes, and having a reduction in the frequency of platelets and leukocytes;
contacting the enriched erythrocyte sample with a first fluorescent reagent that labels GPI anchor-expressing erythrocytes, but not GPI anchor-deficient erythrocytes, and a second fluorescent reagent that specifically labels platelets;
contacting the enriched erythrocyte sample with paramagnetic particles that bind specifically to the first fluorescent reagent of the labeled GPI anchor-expressing erythrocytes and, optionally, the second fluorescent reagent of the labeled platelets;
magnetically separating the enriched erythrocyte sample into a first portion comprising platelets and GPI anchor-expressing erythrocytes and a second portion comprising GPI anchor-deficient erythrocytes;
contacting the enriched erythrocyte sample or the second portion with a third fluorescent reagent that differentially labels normochromatic erythrocytes from reticulocytes and leukocytes;
exciting the first, second, and third fluorescent reagents in the second portion with light of appropriate excitation wavelength, wherein the third fluorescent reagent has a fluorescent emission spectrum that does not substantially overlap with the fluorescent emission spectra of the first or second fluorescent reagents; and
detecting the fluorescent emission and light scatter produced by the GPI anchor-deficient erythrocytes of the second portion labeled with the third fluorescent reagent, while excluding contaminating GPI anchor-expressing erythrocytes and reticulocytes, platelets, and leukocytes, and counting the number of GPI anchor-deficient erythrocytes and reticulocytes relative to the total number of erythrocytes and reticulocytes, respectively, in the enriched erythrocyte sample, wherein a statistically significant deviation in the frequency of GPI anchor-deficient erythrocytes or reticulocytes from a baseline frequency of GPI anchor-deficient erythrocytes or reticulocyte indicates that the agent can modify DNA damage.

20. The method of claim 19 wherein the enriched erythrocyte sample is obtained from a mammal exposed to an agent that may modify mutagenic DNA damage and a known mutagenic DNA damaging agent.

21. A method of assessing mutagenic DNA-damaging potential of an agent, the method comprising:
providing an enriched erythrocyte sample obtained from a mammal exposed to an agent that may induce mutagenic DNA damage, said sample comprising normochromatic erythrocytes and reticulocytes, and having a reduction in the frequency of platelets and leukocytes;
contacting the enriched erythrocyte sample with a first fluorescent reagent that labels GPI anchor-expressing erythrocytes, but not GPI anchor-deficient erythrocytes, and a second fluorescent reagent that specifically labels platelets;
contacting the enriched erythrocyte sample with paramagnetic particles that bind specifically to the first fluorescent reagent of the labeled GPI anchor-expressing erythrocytes and, optionally, the second fluorescent reagent of the labeled platelets;
separating the enriched erythrocyte sample into a first portion comprising labeled GPI anchor-expressing erythrocytes and, optionally, labeled platelets bound to the paramagnetic particles, and a second portion comprising GPI anchor-deficient erythrocytes that are not bound to the paramagnetic particles, by exposing the enriched erythrocyte sample to a magnetic field to recover the second portion;
contacting the enriched erythrocyte sample or the second portion with a third fluorescent reagent that differentially labels normochromatic erythrocytes from reticulocytes and leukocytes;
exciting the first, second, and third fluorescent reagents in the second portion with light of appropriate excitation wavelength, wherein the third fluorescent reagent has a fluorescent emission spectrum that does not substantially overlap with the fluorescent emission spectra of the first or second fluorescent reagents; and
detecting the fluorescent emission and light scatter produced by the GPI anchor-deficient erythrocytes of the second portion labeled with the third fluorescent reagent, while excluding contaminating GPI anchor-expressing erythrocytes and reticulocytes, platelets, and leukocytes, and counting the number of GPI anchor-deficient erythrocytes and reticulocytes relative to the total number of erythrocytes and reticulocytes, respectively, in the enriched erythrocyte sample, wherein a statistically significant deviation in the frequency of GPI anchor-deficient erythrocytes or reticulocytes from a baseline frequency of GPI anchor-deficient erythrocytes or reticulocytes in a sample from an unexposed or vehicle control exposed mammal indicates the mutagenic DNA-damaging potential of the agent.

* * * * *